United States Patent [19]

Sargeant

[11] 4,289,486
[45] Sep. 15, 1981

[54] PNEUMATIC DENTAL SCALER

[75] Inventor: Roger E. Sargeant, Ashford, Conn.

[73] Assignee: Innovate, Inc., Ashford Lake, Conn.

[21] Appl. No.: 142,097

[22] Filed: Apr. 21, 1980

[51] Int. Cl.³ .............................................. A61C 1/07
[52] U.S. Cl. .................................................. 433/118
[58] Field of Search ....................... 433/118, 119, 122

[56] References Cited

U.S. PATENT DOCUMENTS

| 2,751,685 | 6/1956 | Sharon et al. | 433/122 |
| 3,286,558 | 11/1966 | Hufnzgel | 433/118 |
| 3,526,962 | 9/1970 | Fuerst | 433/122 |

Primary Examiner—Robert Peshock
Attorney, Agent, or Firm—Fishman and Van Kirk

[57] ABSTRACT

The tip of a dental scaler is caused to move in a linear path by converting the rotary motion of a pneumatic turbine to periodic vibrations. The turbine will be continuously operating and the vibratory tip drive will be produced only when the tip is urged against a tooth.

8 Claims, 2 Drawing Figures

PNEUMATIC DENTAL SCALER

BACKGROUND OF THE INVENTION:

(1) Field of the Invention

The present invention relates to the field of dentistry and particularly to the removal of plaque from teeth. More specifically, this invention is directed to a dental scaler. Accordingly, the general objects of the present invention are to provide a novel and improved methods and apparatus of such character.

(2) Description of the Prior Art

In the field of dentistry, the removal of plaque from teeth is presently accomplished either manually of with the aid of a power driven tool having a scaling tip which vibrates at a comparatively high frequency. Present "power" scaling tools are typically provided with a separate power supply which includes a radio frequency oscillator and a converter which converts the output of the RF oscillator to mechanical motion at an ultrasonic frequency.

Presently available "power" dental scalers are also characterized by orbital tip motion. Orbital motion is known to be far less desirable than linear chipping action. For example, the orbital motion is characterized by an undesirable degree of heat being produced at the interface of the tip and tooth.

Further disadvantages of the present "power" dental scalers include their comparative complexity, relatively high cost and the fact that care must be taken to insure that the devices are not operated in the presence of a patient having a cardiac pacemaker. A further disadvantage of presently available apparatus, resulting from the comparative complexity thereof, resides in the fact that repair in the dentist's office is usually impossible and removal of the equipment from the office for service is, at best, an annoying inconvenience. A further disadvantage, albeit a comparatively minor problem, resides in the shock hazard incident to the use of any appliance with an electrical power supply.

Continuing to discuss prior art "power" dental scalers, the efficiency of use, and thus the danger of damage to the patient's teeth, is primarily a function of operator skill and training. Restated, presently available apparatus does not include any built-in safety feature which will provide a warning that poor operator technique may be potentially causing tooth damage due, for example, to the application of excessive tip pressure.

SUMMARY OF THE INVENTION:

The present invention overcomes the above briefly discussed and other deficiencies and disadvantages of the prior art by providing a novel and improved fluidically driven dental scaler. Apparatus in accordance with a preferred embodiment of the present invention employs, as its sole power source, the low pressure air customarily available in the dentist's office for the driving of turbine powered drills. In actual fact, a pneumatic dental scaler in accordance with the present invention may be provided in the form of a hand piece which is capable of being coupled to existing equipment.

Apparatus in accordance with a preferred embodiment of the present invention is characterized by very few moving parts. These moving parts constitute a scaling tip drive wherein motion is imparted to the tip only when contact between the tip and a patient's tooth is established. When such contact is established, the tip will vibrate, with the direction of motion being generally linear, at a frequency of, by way of example only, 30,000 oscillations per second within a stroke of, again by way of example, 0.007 inches at the cutting tip. This vibratory tip motion is derived from a conventional pneumatic turbine which forms part of the hand piece comprising the preferred embodiment of the invention. The rotary motion of the turbine output shaft is coupled, via an irregularly shaped bumper mounted on the shaft, to a "cup" mounted on a first end of a pivotally mounted drive rod. Resilient means are provided to normally center the "cup" whereby the bumper may rotate without establishing contact with a cooperating contact surface on the interior of the "cup" when the drive rod is in a centralized, undeflected position. Application of pressure to the tip will cause the drive rod to pivot whereby periodic contact will be established between the bumper on the turbine output shaft and the cooperating surface of the "cup" and the rotation of the turbine will be converted into vibratory tip motion.

BRIEF DESCRIPTION OF THE DRAWING:

The present invention may be better understood and its numerous objects and advantages will become apparent to those skilled in the art by reference to the accompanying drawing wherein like reference numerals refer to like elements in the two figures and in which.

Figure 1:
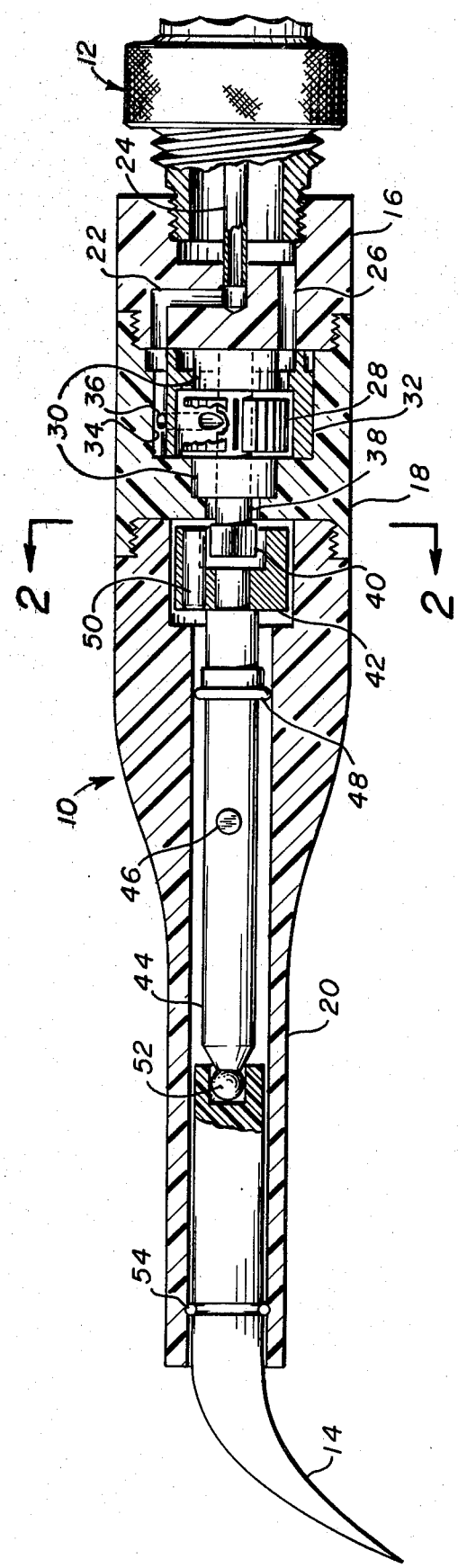
FIG. 1 is a cross-sectional, side elevation view of a pneumatic dental scaler in accordance with a first embodiment of the present invention.

DESCRIPTION OF THE PREFERRED EMBODIMENT:

With reference now to the drawing, an improved pneumatic dental scaler in accordance with the present invention is indicated generally at 10. The dental scaler 10 produces, from low pressure drive air supplied via a fitting indicated generally at 12, oscillatory motion of a scaling tip 14. The dental scaler 10 is in the form of a hand piece which, in the disclosed embodiment, consists of three molded plastic sections 16, 18 and 20. In the disclosed embodiment these three sections are threadably engaged with one another. Hand piece section 16 receives the above mentioned conventional fitting 12 and, in part, defines the flow paths for the drive air and exhaust. Thus, hand piece section 16 includes a drive air passage 22 which communicates, at its upstream end, with a nipple 24. Nipple 24, in turn, is mated with the drive air supply conduit in fitting 12. Hand piece section 16 also includes an exhaust passage 26 which communicates, at its downstream end, with a plenum chamber defined in part by the fitting receiving recess in the base of section 16.

Hand piece section 18 provides a housing for a conventional pneumatic turbine. Turbine 28 rotates on bearings 30 which are press fit onto the turbine shaft and received in an axial bore defined by the body of section 18 and a plastic insert 32. The air for driving turbine 28 is delivered via a passage 34 which is aligned within and in communication with the passage 22 in hand piece section 16. Passage 34 is provided with one or more transverse ports 36 whereby the pressurized air supplied via passages 22 and 34 may be directed against the blades of turbine 28. The delivery of pressurized air to hand piece 10 via the coupling 12 will, accordingly, cause turbine 28 to rotate. In one reduction to practice of the invention, with the supply air being at 50 psi, turbine 28 rotated at 400, 000 RPM.

Turbine 28 has an output shaft 38 which extends into an axial bore provided in hand piece section 20. A rectangular bumper 40 is press fit on the free end of turbine shaft 38 and thus rotates with the turbine. In the preferred embodiment, as may be seen by joint consideration of FIGS. 1 and 2, bumper 40 is square. The turbine output shaft 30 will typically be comprised of steel while the bumper 40 will typically be comprised of case hardened steel. If necessary, bumper 40 may be keyed to shaft 38 to prevent relative rotation therebetween.

Bumper 40 is received within a cup 42 which is press fit on a first end of a pivotally mounted drive rod 44. Drive rod 44 is positioned within an axial bore in hand piece section 20. For reasons which will become apparent from the description below, drive rod 44 is mounted for rotation about a pin 46 which functions as a fulcrum; pin 46 extending through the body of hand piece section 20. With drive rod 44 in its undeflected position as shown, there will be clearance between bumper 40, about its entire periphery, and the inside of the cup 42 and thus rod 44 will remain motionless although the turbine 28 is rotating. This "rest" or central position of rod 44, and thus of cup 42, is established by means of a ring 48 of rubber or other suitable resilient material installed on rod 44 at the cup side of fulcrum 46.

Figure 2:
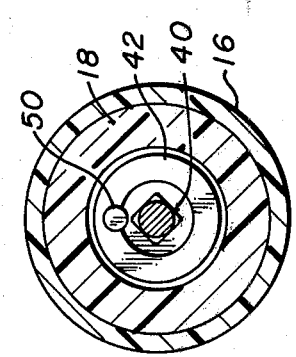
FIG. 2 is a view taken along line 2—2 of FIG. 1.

As may best be seen from joint consideration of FIGS. 1 and 2, cup 42, which may be comprised of polytetrafluoroethylene, but which is preferably comprised of steel, is provided with an off-center cylindrical bore which receives a case hardened steel dowel 50. An arcuate section of dowel 50 extends into the interior of cup 42 so as to be juxtapositioned to, but normally out of contact with, those portions of bumper 40 which have the maximum radii.

The drive rod 44, at the end opposite to that which supports cup 42, is provided with a ball-type member 52. As shown in FIG. 1, ball 52 will engage a cylindrical blind hole in the base of the scaling tip 14 to form a ball joint between the drive rod and tip. The hand piece section 20 will, adjacent the forward edge of the axial bore therethrough, be provided with an annular recess which receives a rubber O-ring 54 installed on tip 14. The O-ring 54 serves as the fulcrum about which the tip 14 moves during the oscillatory motion thereof produced in the manner to be described below.

In use, when tip 14 is moved into contact with a tooth, the tip will pivot about O-ring 54. This pivotal motion of tip 54 will, via the ball-and-socket arrangement including ball 52, be transmitted to drive rod 44 thus causing rod 44 to pivot about pin 46 against the resilient recoil or restoring force of ring 48. Cup 42 will, accordingly, move out of its normally centered position whereby contact will be established between the corners of the rotating bumper 40 and the protruding surface of dowel 50. Accordingly, for each rotation of turbine 28, depending on the shape of bumper 40, cup 42 will be caused to transcribe one or more excursions which, considering the preferred embodiment as disclosed in FIG. 1, will generally be in the plane of the paper. These excursions, which approach being linear in direction, are transmitted via rod 44 to tip 14; i.e., the tip will oscillate about an axis which is transverse to the axis of O-ring 54. A particularly important aspect of the present invention is that tip 14 is constrained to move in a generally linear path, rather then undergoing orbital motion as has characterized prior art power driven scalers, by the pivot pin 46.

A further particularly desirable and unique feature of the present invention resides in the fact that the pressure applied to the patient's tooth is directly transduced into an audible sound which may be interpreted by the technician. That is, excessive tip pressure will load turbine 28 and will be immediately apparent as a change in the sound produced by the turbine. This provides a built-in safety feature which may prevent harm resulting from poor operator technique.

While a preferred embodiment has been shown and described, various modifications and substitutions may be made thereto without departing from the spirit and scope of the invention. Thus, by way of example only, various alternative means may be provided to impart the restoring force to drive rod 44 and such resilient means may be located at either side of the pin 46. Accordingly, it is to be understood that the present invention has been described by way of illustration and not limitation.

What is claimed is:

1. Dental apparatus comprising:
   means for converting a flow of fluid to an output shaft rotation;
   means for engaging and driving a dental tool, said driving means including a pivotally mounted elongated drive shaft, said drive shaft engaging a tool at its first end, said drive shaft first end being constrained by the pivot mounting to move linearly;
   means for translating said converting means output shaft rotation to periodic movement of said driving means shaft about its pivot mounting, said translating means including an irregularly shaped member mounted on said converting means output shaft for rotation therewith, said translating means further including a contact member extending from the second end of said driving means shaft in juxtapositioned relationship to said irregularly shaped member; and
   means resiliently biasing said driving means shaft to a position where there is clearance between said contact member and said irregularly shaped member during rotation of said irregularly shaped member, the application of force to the first end of said diving means shaft overcoming the resilient bias and causing said shaft to pivot whereby the second end of said shaft and said contact member are deflected and the portions of said irregularly shaped member having maximum radius will periodically engage said contact member to thereby urge said drive shaft against the resilient bias to impart vibratory motion to a tool engaged by the first end of said drive shaft.

2. The apparatus of claim 1 wherein said translating means contact member comprises:
   cup means defining a recess for receiving said irregularly shaped member; and
   a contact element supported by said cup means and extending into the recess defined thereby so as to be in close proximity to but normally out of contact with said irregularly shaped member, deflection of said driving means shaft causing the establishment of contact between said contact element and said irregularly shaped member.

3. The apparatus of claim 1 wherein said converting means comprises:

a pneumatic turbine, said irregularly shaped member being mounted on the turbine shaft.

4. The apparatus of claim 1 further comprising:

housing means, said housing means defining a variable diameter bore, said driving means shaft being positioned in said bore and pivoting about a pin supported in said housing means intermediate the ends of said shaft.

5. The apparatus of claim 4 wherein said resilient biasing means comprises:

a ring of resilient material installed on said driving means shaft, said ring cooperating with the walls of the bore in said housing means to apply a restoring force to said shaft when the second end thereof is deflected as a result of contact between said rotating irregularly shaped member and said contact member.

6. The apparatus of claim 4 wherein the first end of said drive means shaft defines a portion of a ball joint and wherein said apparatus further comprises:

a dental tool, said tool comprising a tip portion intended for use in the removal of plaque from teeth, said tip further comprising a cylindrical second end portion extending from said tip portion, the end of said cylindrical portion having a socket formed therein for engagement with said drive shaft ball joint portion whereby said shaft will drive said tip; and means positioned intermediate the ends of said second portion of said tool and defining a surface about which said tool may pivot.

7. The apparatus of claim 6 wherein said translating means contact member comprises:

cup means defining a recess for receiving said irregularly shaped member; and a contact element supported by said cup means and extending into the recess defined thereby so as to be in close proximity to but normally out of contact with said irregularly shaped member, deflection of said driving means shaft causing the establishment of contact between said contact element and said irregularly shaped member.

8. The apparatus of claim 7 wherein said resilient biasing means comprises:

a ring of resilient material installed on said driving means shaft, said ring cooperating with the walls of the bore in said housing means to apply a restoring force to said shaft when the second end thereof is deflected as a result of contact between said rotating irregularly shaped member and said contact member.

* * * * *